United States Patent
Takeda (10) Patent No.: US 11,096,669 B2
(45) Date of Patent: Aug. 24, 2021

(54) ULTRASOUND DIAGNOSTIC APPARATUS, ULTRASOUND IMAGE GENERATION METHOD AND STORAGE MEDIUM

(71) Applicant: Konica Minolta, Inc., Tokyo (JP)

(72) Inventor: Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 370 days.

(21) Appl. No.: 16/171,868

(22) Filed: Oct. 26, 2018

(65) Prior Publication Data

US 2019/0125310 A1 May 2, 2019

(30) Foreign Application Priority Data

Oct. 31, 2017 (JP) .............................. JP2017-210313

(51) Int. Cl.
| | |
|---|---|
| *A61B 8/00* | (2006.01) |
| *A61B 8/08* | (2006.01) |
| *A61B 8/14* | (2006.01) |
| *A61B 8/06* | (2006.01) |
| *G01S 15/89* | (2006.01) |

(52) U.S. Cl.
CPC .............. *A61B 8/5207* (2013.01); *A61B 8/06* (2013.01); *A61B 8/14* (2013.01); *A61B 8/46* (2013.01); *A61B 8/488* (2013.01); *A61B 8/5269* (2013.01); *G01S 15/8977* (2013.01); *G01S 15/8981* (2013.01); *A61B 8/463* (2013.01); *A61B 8/469* (2013.01); *A61B 8/5246* (2013.01)

(58) Field of Classification Search
CPC combination set(s) only.
See application file for complete search history.

(56) References Cited

U.S. PATENT DOCUMENTS

| | | | | |
|---|---|---|---|---|
| 2011/0137174 A1* | 6/2011 | Park | ................... | G01S 15/8981 600/454 |
| 2015/0366540 A1* | 12/2015 | Sato | ...................... | A61B 8/461 600/453 |
| 2017/0071569 A1* | 3/2017 | Sato | ................... | G01S 15/8963 |

FOREIGN PATENT DOCUMENTS

JP      2014158698 A      9/2014

\* cited by examiner

*Primary Examiner* — Joel F Brutus
(74) *Attorney, Agent, or Firm* — Cantor Colburn LLP (57) ABSTRACT

An ultrasound diagnostic apparatus includes a transmitter, a receiver and a hardware processor. The transmitter outputs a drive signal for a C-mode image to an ultrasound probe. The receiver obtains a reception signal from the probe. The processor sets at least one mask in a frame of packet data of the reception signal; calculates a covariance matrix from a plurality of packet data included in the mask; calculates an eigenvector for the mask from the covariance matrix; calculates a first filter coefficient for the packet data by using the eigenvector and a gain matrix; performs interpolation on the first filter coefficient to calculate a second filter coefficient for packet data of each position in the frame; filters the packet data of the position by using the second filter coefficient; and generates C-mode image data from the filtered packet data.

9 Claims, 9 Drawing Sheets

OUTPUT VECTOR y    FILTER MATRIX A $n \times n$ MATRIX    INPUT VECTOR x $n \times 1$ MATRIX

FIG.5

$A_{reg}$ = ORTHONORMAL BASIS b ($n \times n$ MATRIX) × GAIN MATRIX G ($n \times n$ MATRIX) × ORTHONORMAL BASIS $b^H$ ($n \times n$ MATRIX)

→ DEGREE     ↓ DEGREE

| UI DISPLAY NUMBER | SPACE BETWEEN MASKS | NUMBER OF MASKS | MASK SIZE | CLUTTER REMOVAL STRENGTH |
|---|---|---|---|---|
| 1 | WIDE | FEW | LARGE | WEAK |
| 2 | MODERATE | MODERATE | MODERATE | MODERATE |
| 3 | NARROW | MANY | SMALL | STRONG |

FIG.8B

| UI DISPLAY NUMBER | SPACE BETWEEN MASKS | NUMBER OF MASKS | MASK SIZE | FRAME RATE |
|---|---|---|---|---|
| 1 | NARROW | MANY | SMALL | LOW |
| 2 | MODERATE | MODERATE | MODERATE | MODERATE |
| 3 | WIDE | FEW | LARGE | HIGH |

ULTRASOUND DIAGNOSTIC APPARATUS, ULTRASOUND IMAGE GENERATION METHOD AND STORAGE MEDIUM

CROSS REFERENCE TO RELATED APPLICATION

The present application claims priority under 35 U.S.C. § 119 to Japanese Application No. 2017-210313, filed Oct. 31, 2017, the entire content of which is incorporated herein by reference.

BACKGROUND

1. Technological Field

The present invention relates to an ultrasound diagnostic apparatus, an ultrasound image generation method and a storage medium.

2. Description of the Related Art

Ultrasound diagnosis is popular because heartbeat, movement of a fetus, or the like can be obtained as ultrasound images by simple operation of putting an ultrasound probe on the body surface and also because this examination can be repeatedly performed thanks to its high level of safety. There is known an ultrasound diagnostic apparatus which generates and displays ultrasound images for ultrasound diagnosis.

Figure 12:
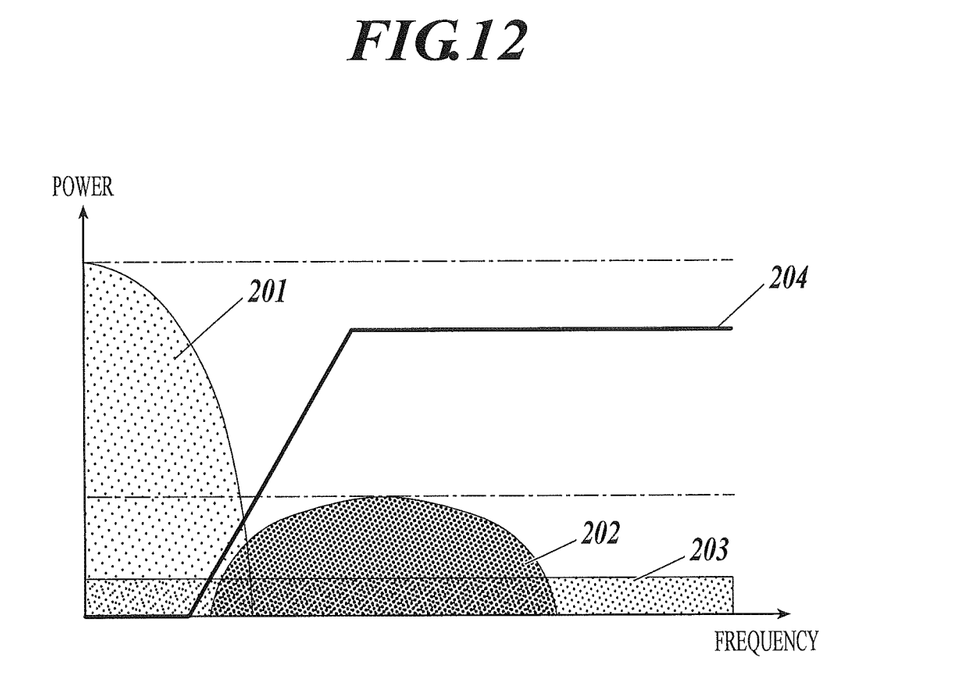
FIG. 12 shows packet data and frequency characteristics of power of a conventional MTI filter.

Further, there is known an ultrasound diagnostic apparatus which transmits and receives ultrasound to and from a test object, generates C (color flow (color Doppler))-mode images in which blood flow of the test object is shown in color by Doppler method, and displays the same. FIG. 12 shows packet data and frequency characteristics of power of a conventional MTI (Moving Target Indication) filter.

If, in generating C-mode image data, frequency characteristics of power of Doppler signal(s) (packet data) corresponding to reception signal(s) based on ultrasound reflected by a test object are obtained, as shown in FIG. 12, the packet data is composed of a clutter component 201, a blood flow component 202 and a noise component 203. The clutter component 201 is a signal component of movement of tissue of the test object. The blood flow component 202 is a signal component of the blood flow of the test object. The noise component 203 is a signal component of system noise (random noise) inherent in apparatuses.

In order to visualize the blood flow component in a C-mode image, of the Doppler signal, the clutter component 201 is removed by an MTI filter 204. The MTI filter 204 is a high-pass filter which removes the clutter component and extracts a Doppler shift component only.

There is also known an ultrasound diagnostic apparatus using an eigenvector MTI filter which performs principle component analysis by using a correlation matrix(es), approximates an eigenvector component with a large eigenvalue as the clutter component, and removes the same from packet data, thereby removing clutter. (Refer to JP 2014-158698 A.) In JP 2014-158698 A, there are described: a first embodiment in which one correlation matrix is calculated for the entire scan region where the blood flow is displayed, and the same MTI filter is applied to the entire image; and a second embodiment in which a coefficient for the eigenvector MTI filter is calculated by performing spatial interpolation on correlation matrixes calculated for respective processing blocks.

For the ultrasound diagnostic apparatus utilizing a conventional eigenvector MTI filter, there are two usable methods as an eigenvector MTI filtering method. One is, as described in the first embodiment in JP 2014-158698 A, a method [1] of generating a correlation matrix from packet data on the entire frame; and performing one eigenvector MTI filtering thereon. The other is, as described in the second embodiment in JP 2014-158698 A, a method [2] of generating correlation matrixes about respective packet data, thereby generating eigenvector MTI filters; and performing different eigenvector MTI filtering thereon.

In the case of the method [1], the clutter component locally generated cannot be estimated, and accordingly clutter removal performance is often insufficient. In the case of the method [2], it is necessary to, for each packet data, keep an n×n complex correlation matrix, perform eigenvalue analysis and calculate a filter coefficient. In matrix eigenvalue calculation, the calculation amount increases in proportion to the cube of a dimension(s) (the number of elements per line) of a matrix. Hence, in order to keep the n×n complex correlation matrix for each packet data, a massive memory amount is necessary, and also, in order to perform eigenvalue analysis on each thereof, a very high-speed arithmetic unit is necessary. It is, therefore, impossible for an existing machine to realize the [2], and accordingly its performance must be equivalent to the [1].

Further, in the case where CFM (Color Flow Mapping) is performed by a high-frame-rate method described in JP 2014-158698 A, the number of dimensions n of a correlation function is likely to increase in the future, and hence there is a demand for increase in efficiency of calculation cost.

SUMMARY

Objects of the present invention include reducing calculation cost and keeping high clutter removal performance in an adaptive MTI filter using eigenvectors.

In order to achieve at least one of the abovementioned objects, according to a first aspect of the present invention, there is provided an ultrasound diagnostic apparatus including: a transmitter which generates a drive signal for a C-mode image and outputs the drive signal to an ultrasound probe which transmits and receives ultrasound; a receiver which obtains a reception signal from the ultrasound probe; and a hardware processor which: sets at least one mask in a frame of packet data of the reception signal; calculates a covariance matrix from a plurality of packet data included in the mask of the reception signal; calculates an eigenvector for the mask from the calculated covariance matrix; calculates a first filter coefficient for the packet data of the mask by using the calculated eigenvector and a gain matrix; performs interpolation on the calculated first filter coefficient so as to calculate a second filter coefficient for packet data of each position in the frame; filters the packet data of the position by using the calculated second filter coefficient; and generates C-mode image data from the filtered packet data.

According to a second aspect of the present invention, there is provided an ultrasound image generation method including: generating a drive signal for a C-mode image and outputting the drive signal to an ultrasound probe which transmits and receives ultrasound; obtaining a reception signal from the ultrasound probe; setting at least one mask in a frame of packet data of the reception signal; calculating a covariance matrix from a plurality of packet data included in the mask of the reception signal; calculating an eigenvector for the mask from the calculated covariance matrix; calculating a first filter coefficient for the packet data of the mask by using the calculated eigenvector and a gain matrix; performing interpolation on the calculated first filter coefficient so as to calculate a second filter coefficient for packet data of each position in the frame; filtering the packet data of the position by using the calculated second filter coefficient; and generating C-mode image data from the filtered packet data.

According to a third aspect of the present invention, there is provided a non-transitory computer readable storage medium storing a program to cause, of an ultrasound diagnostic apparatus including: a transmitter which generates a drive signal for a C-mode image and outputs the drive signal to an ultrasound probe which transmits and receives ultrasound; and a receiver which obtains a reception signal from the ultrasound probe, a computer to: set at least one mask in a frame of packet data of the reception signal; calculate a covariance matrix from a plurality of packet data included in the mask of the reception signal; calculate an eigenvector for the mask from the calculated covariance matrix; calculate a first filter coefficient for the packet data of the mask by using the calculated eigenvector and a gain matrix; perform interpolation on the calculated first filter coefficient so as to calculate a second filter coefficient for packet data of each position in the frame; filter the packet data of the position by using the calculated second filter coefficient; and generate C-mode image data from the filtered packet data.

BRIEF DESCRIPTION OF THE DRAWINGS

The advantages and features provided by one or more embodiments of the present invention will become more fully understood from the detailed description given hereinbelow and the appended drawings which are given by way of illustration only, and thus are not intended as a definition of the limits of the present invention, wherein.

DETAILED DESCRIPTION OF EMBODIMENTS

Hereinafter, one or more embodiments of the present invention will be described in detail with reference to the drawings. However, the scope of the present invention is not limited to the disclosed embodiments or the drawings.

Figure 1:
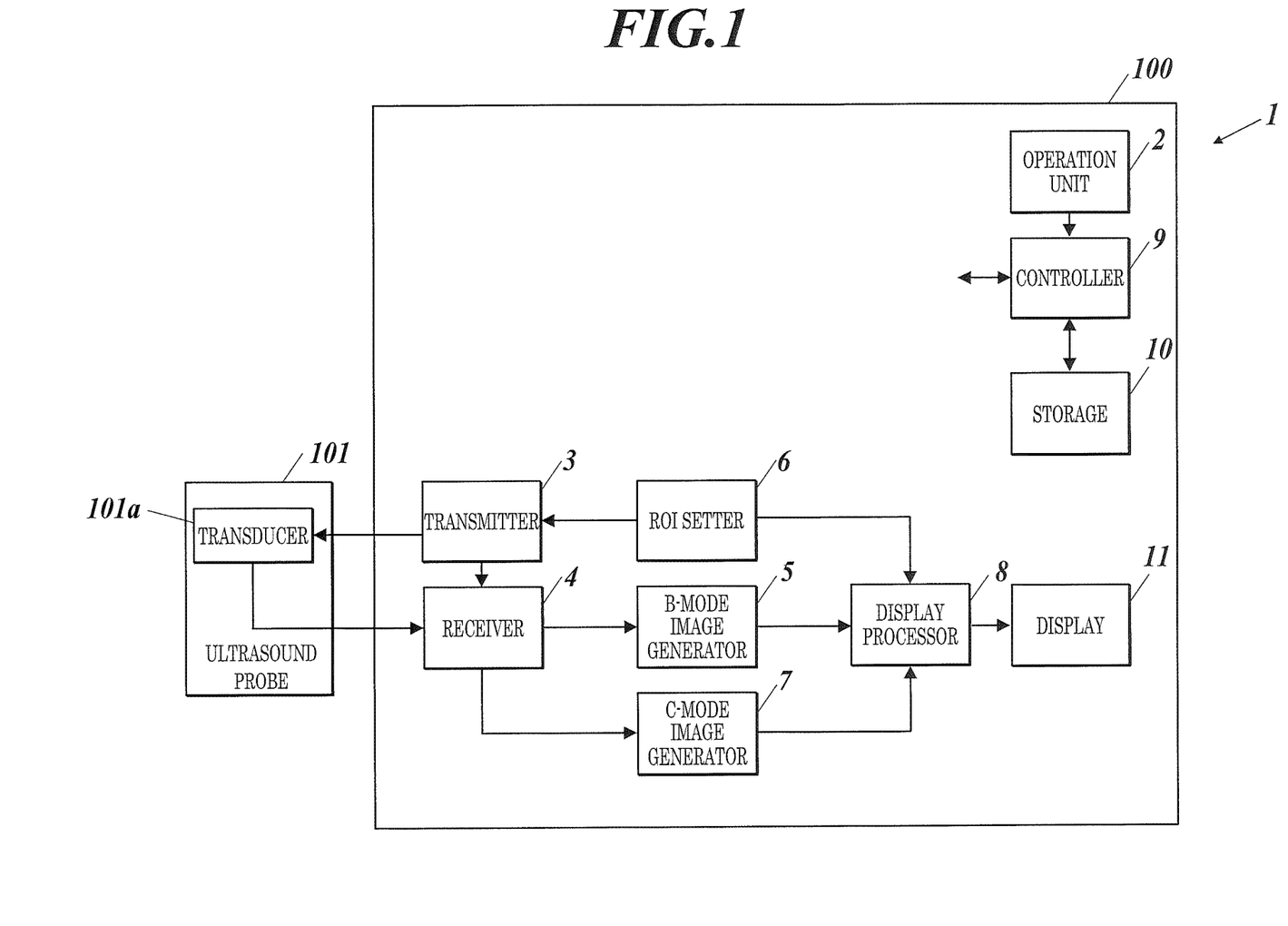
FIG. 1 is a block diagram schematically showing configuration of an ultrasound diagnostic apparatus according to an embodiment(s) of the present invention.
Figure 2:
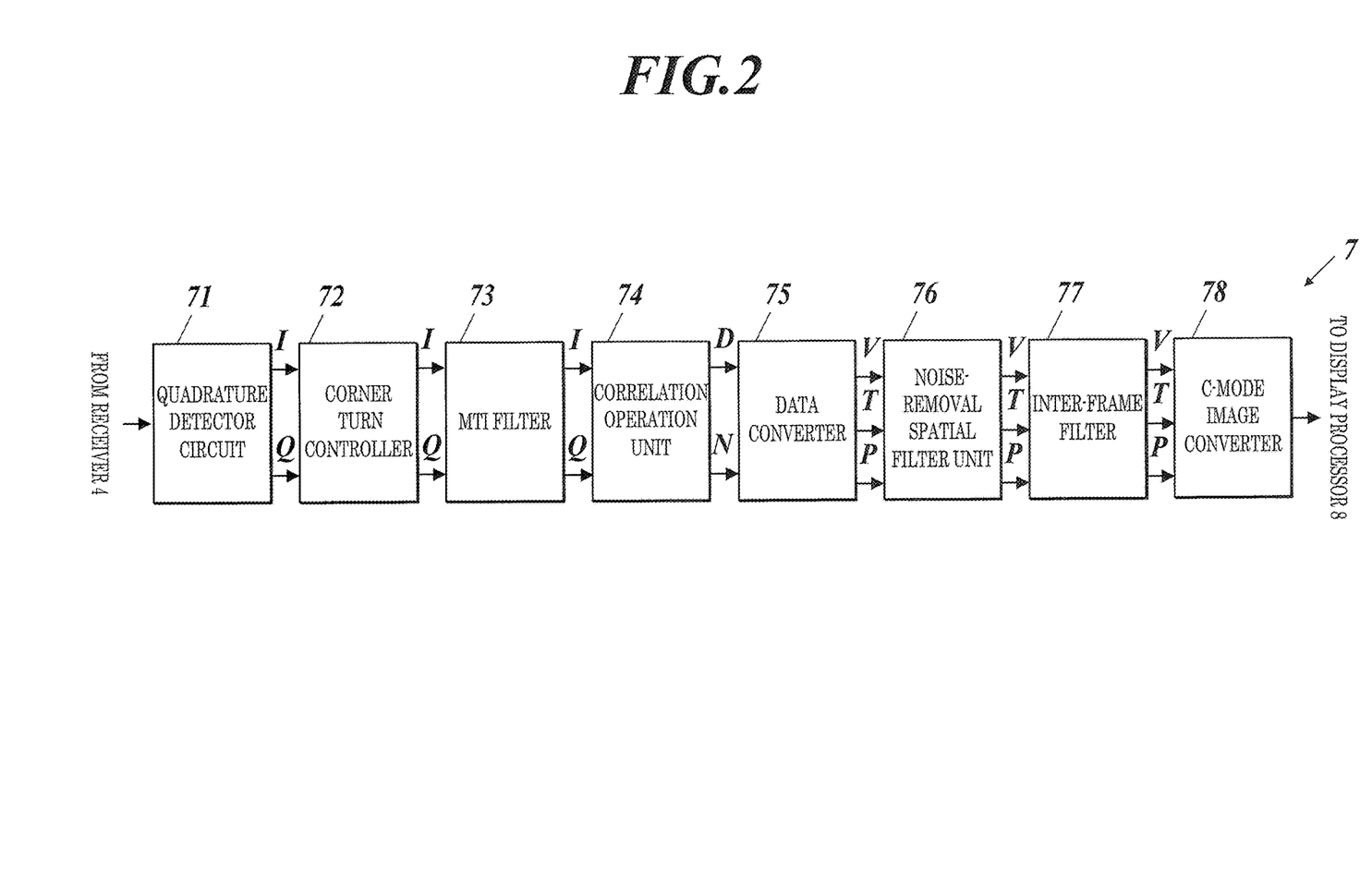
FIG. 2 is a block diagram showing functional configuration of a C-mode image generator.
Figure 3:
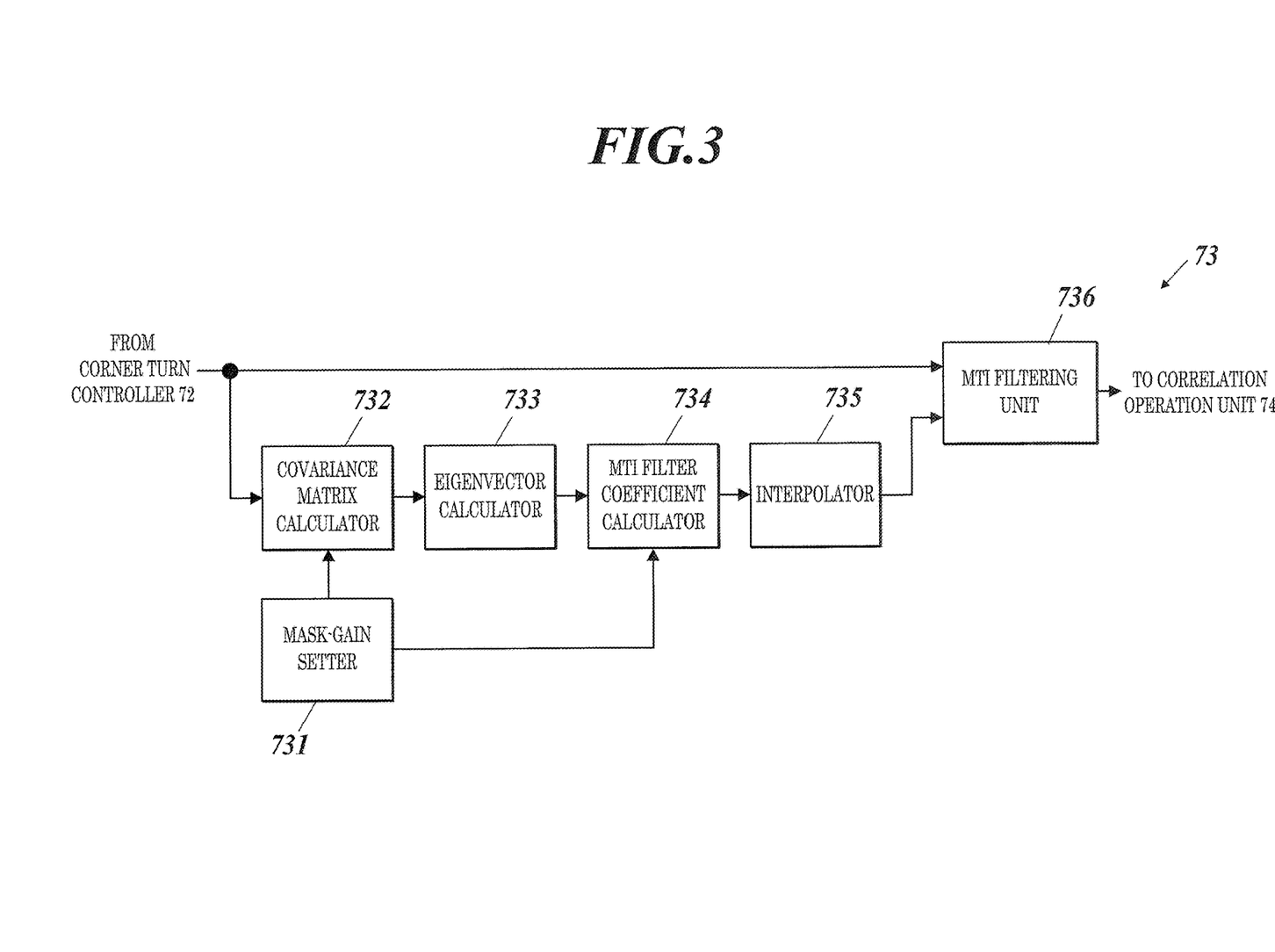
FIG. 3 is a block diagram showing functional configuration of an MTI filter.

First, with reference to FIG. 1 to FIG. 3, configuration of an apparatus according to an embodiment(s) is described. FIG. 1 is a block diagram schematically showing configuration of an ultrasound diagnostic apparatus 1 according to this embodiment. FIG. 2 is a block diagram showing functional configuration of a C-mode image generator 7. FIG. 3 is a block diagram showing functional configuration of an MTI filter 73.

The ultrasound diagnostic apparatus 1 shown in FIG. 1 is installed in a medical facility, such as a hospital, and generates ultrasound images of a test object, such as an organ of a patient, as an object to be measured. The ultrasound diagnostic apparatus 1 is configured such that a body 100 is connected with an ultrasound probe 101.

The body 100 includes an operation unit 2, a transmitter 3, a receiver 4, a B (Brightness)-mode image generator 5, an ROI (Region of Interest) setter 6, a C-mode image generator 7, a display processor 8, a controller 9, a storage 10 and a display 11.

The ultrasound probe 101 has a plurality of transducers (piezoelectric transducers) 101a which are arranged one-dimensionally. The transducers 101a each convert drive signal(s) (transmission electric signal) transmitted from the transmitter 3, described below, into ultrasound, thereby generating ultrasound beams. A user puts the ultrasound probe 101 on the surface of the test object, so that the ultrasound beams can be emitted into the test object. The ultrasound probe 101 receives reflected ultrasound from the inside of the test object, converts, with the transducers 101a, the reflected ultrasound into reception electric signal(s), and supplies the signal to the receiver 4 described below.

In this embodiment, the ultrasound probe 101 is a linear ultrasound probe 101 in which transducers 101a are arranged one-dimensionally. However, this is not intended to limit the present invention. For example, a convex ultrasound probe 101 or a sector ultrasound probe 101 in which transducers 101a are arranged one-dimensionally, an ultrasound probe 101 in which transducers 101a are arranged two-dimensionally, an ultrasound probe 101 in which transducers 101a arranged one-dimensionally swing, or the like can be used. Further, under the control of the controller 9, the transmitter 3 selects transducers 101a to be used by the ultrasound probe 101, and changes, for each transducer 101a, timing at which voltage is applied and a value of the voltage, so that an irradiation position and an emission direction of ultrasound to be transmitted by the ultrasound probe 101 can be controlled.

The ultrasound probe 101 may have some of functions of the transmitter 3 and the receiver 4 described below. For example, the ultrasound probe 101 generates, on the basis of control signal(s) (hereinafter "transmission control signal") for generating drive signal(s) output from the transmitter 3, the drive signal in itself, and converts, with the transducers 101a, the drive signal into ultrasound, and also converts, with the transducers 101a, the received reflected ultrasound into the reception electric signal, and generates, on the basis of the reception electric signal, reception signal(s), described below, in itself.

In general, the ultrasound probe 101 is electrically connected with the body 100 via a cable. However, this is not intended to limit the present invention. For example, the ultrasound probe 101 may be configured to transmit and receive the transmission signal and the reception signal to and from the body 100 by wireless communications by UWB (Ultra Wide Band) or the like. In this case, needless to say, the body 100 and the ultrasound probe 101 have communication units which can perform wireless communications.

The operation unit 2 accepts inputs from the user, and outputs commands based on the user's inputs to the controller 9. The operation unit 2 has a function for the user to choose a mode (hereinafter "B mode") of displaying only a B-mode image(s) in which amplitude of the reflected ultrasound is expressed by brightness or a mode (hereinafter "C mode") for superimposing and displaying a C (Color flow)-mode image(s) on the B-mode image(s). The operation unit 2 also has a function to accept an input from the user to specify a position of an ROI where the C-mode image is displayed on the B-mode image. As the C-mode image to be displayed, there are C-mode images in display modes which are: a V mode for displaying, in color, flow speed and direction of the blood flow by a blood flow velocity V as a blood flow signal(s) indicating a condition of the blood flow; a P mode for displaying, in color, blood flow power by power P of the blood flow as the blood flow signal; and a V-T mode for displaying, in color, the flow speed and variance of the blood flow by the blood flow velocity V and variance T as the blood flow signal. When accepting an input for the C mode from the user, the operation unit 2 also accepts an input for its display mode. The display modes for C-mode images may include a T (variance) mode and a dP (directional power) mode, for example. Thus, the C mode includes a color Doppler mode (V mode, V-T mode, etc.) and a power Doppler mode (P mode, etc.).

The operation unit 2 may include a touchscreen which is disposed on the display screen of the display 11 and accepts user's touch inputs.

The transmitter 3 at least performs a transmission process for causing the ultrasound probe 101 to transmit ultrasound beams by generating the drive signal. For example, the transmitter 3 performs the transmission process of generating the drive signal for transmitting ultrasound beams from the ultrasound probe 101 having the transducers 101a, and supplies high-voltage drive signal(s) to the ultrasound probe 101, the high-voltage drive signal(s) being generated at predetermined timing(s) on the basis of the drive signal(s), thereby driving the transducers 101a of the ultrasound probe 101. In this way, the ultrasound probe 101 converts the drive signal into ultrasound, thereby emitting ultrasound beams to the test object.

If the C mode is on, under the control of the controller 9, the transmitter 3 performs the transmission process for displaying the C-mode image in addition to the transmission process for displaying the B-mode image. For example, after supplying the electric drive signal for displaying the B-mode image, the transmitter 3 repeatedly supplies the drive signal for displaying the C-mode image in the same direction (to the same line) n (a dozen or so, for example, 16) times with respect to all directions (all lines) of the ROI set by the ROI setter 6. Further, the transmitter 3 specifies, at the time of the transmission process, additional information on the transmission process for the B-mode image or the transmission process for the C-mode image, and supplies this additional information to the receiver 4.

Under the control of the controller 9, the receiver 4 performs a reception process of generating the reception signal as an electric RF (Radio Frequency) signal based on the reflected ultrasound. For example, the receiver 4 generates the reception signal (acoustic data) by amplifying the reception electric signal into which the reflected ultrasound received by the ultrasound probe 101 has been converted thereby and performing A/D conversion and phasing-addition thereon.

The receiver 4 obtains the additional information from the transmitter 3, and supplies the reception signal to the B-mode image generator 5 if the obtained additional information is additional information for the B-mode image, or supplies the reception signal to the C-mode image generator 7 if the obtained additional information is additional information for the C-mode image. Hereinafter, the reception signal for generating the B-mode image and the reception signal for generating the C-mode image are referred to as "B-mode reception signal" and "C-mode reception signal", respectively.

In this embodiment, the receiver 4 determines whether the generated reception signal for image frames are for the B-mode image or the C-mode image, and supplies the same to the block concerned. However, this is not intended to limit the present invention. For example, the B-mode image generator 5 and the C-mode image generator 7 may make the determination about the generated reception signal for image frames.

Under the control of the controller 9, the B-mode image generator 5 generates B-mode image data by performing envelope detection, logarithmic compression and so forth on the B-mode reception signal input from the receiver 4, and adjusting a dynamic range and gain, thereby performing brightness conversion, and outputs the generated B-mode image data to the display processor 8.

Under the control of the controller 9, the ROI setter 6 sets the ROI for the C-mode image into the transmitter 3 and the display processor 8 in accordance with ROI specifying information input by the user via the operation unit 2.

Under the control of the controller 9, the C-mode image generator 7 generates C-mode image data in response to the C-mode reception signal input from the receiver 4, and outputs the generated C-mode image data to the display processor 8. With reference to FIG. 2, internal configuration of the C-mode image generator 7 is described. As shown in FIG. 2, the C-mode image generator 7 includes a quadrature detector circuit 71, a corner turn controller 72, an MTI filter 73, a correlation operation unit 74, a data converter 75, a noise-removal spatial filter unit 76, an inter-frame filter 77 and a C-mode image converter 78.

Under the control of the controller 9, the quadrature detector circuit 71 performs quadrature detection on the C-mode reception signal input from the receiver 4, calculates a phase difference between the obtained C-mode reception signal and a reference signal, and obtains (complex) Doppler signals I, Q.

Under the control of the controller 9, the corner turn controller 72 arranges and then stores into a memory (not shown) the Doppler signals I, Q input from the quadrature detector circuit 71 in a depth direction from the ultrasound probe 101 to the test object and in an ensemble direction of the number of repetition (the number of repeats) n of transmission and reception of ultrasound for each same acoustic line (line), and reads the Doppler signals I, Q in the ensemble direction for each depth.

The reception signal (Doppler signals I, Q) contains unnecessary information (clutter component) on blood vessel wall, tissue and so forth in addition to the blood flow signal component, which is necessary to generate the C-mode image. Under the control of the controller 9, the MTI filter 73 filters the Doppler signals I, Q input from the corner turn controller 72, thereby removing the clutter component.

With reference to FIG. 3, internal configuration of the MTI filter 73 is described. As shown in FIG. 3, the MTI filter 73 includes a mask-gain setter 731, a covariance matrix calculator 732, an eigenvector calculator 733, an MTI filter coefficient calculator 734, an interpolator 735 and an MTI filtering unit 736.

The MTI filter 73 is an MTI filter utilizing orthonormal bases. The orthonormal bases are, for example, eigenvectors obtained, for example, by various orthogonal polynomials and principal component analysis. The orthogonal polynomials include, for example, Legendre polynomial.

Figure 4:
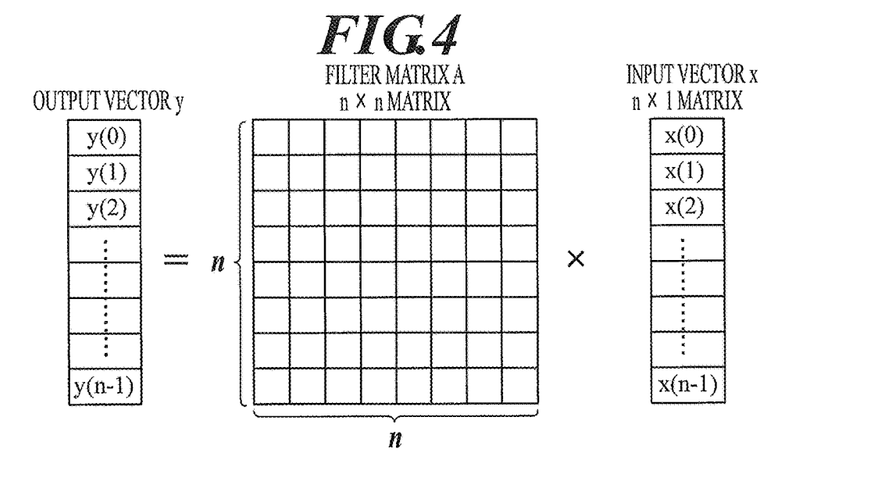
FIG. 4 shows a relationship between input and output of the MTI filter.
Figure 5:
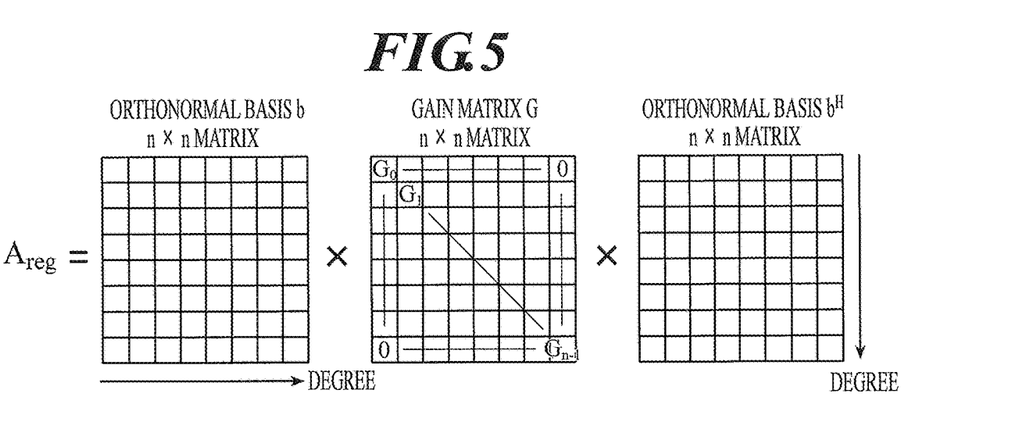
FIG. 5 shows an MTI filter coefficient using orthonormal bases.
Figure 6:
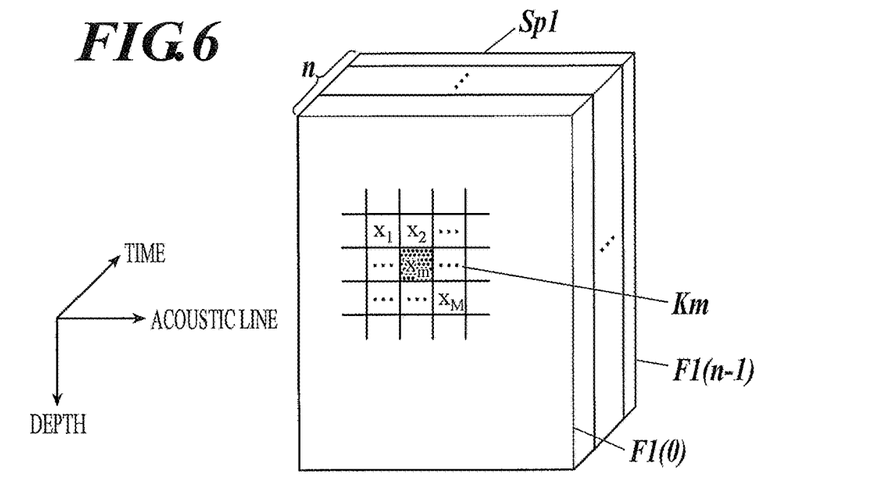
FIG. 6 shows packet data having a packet size n on one frame.
Figure 7:
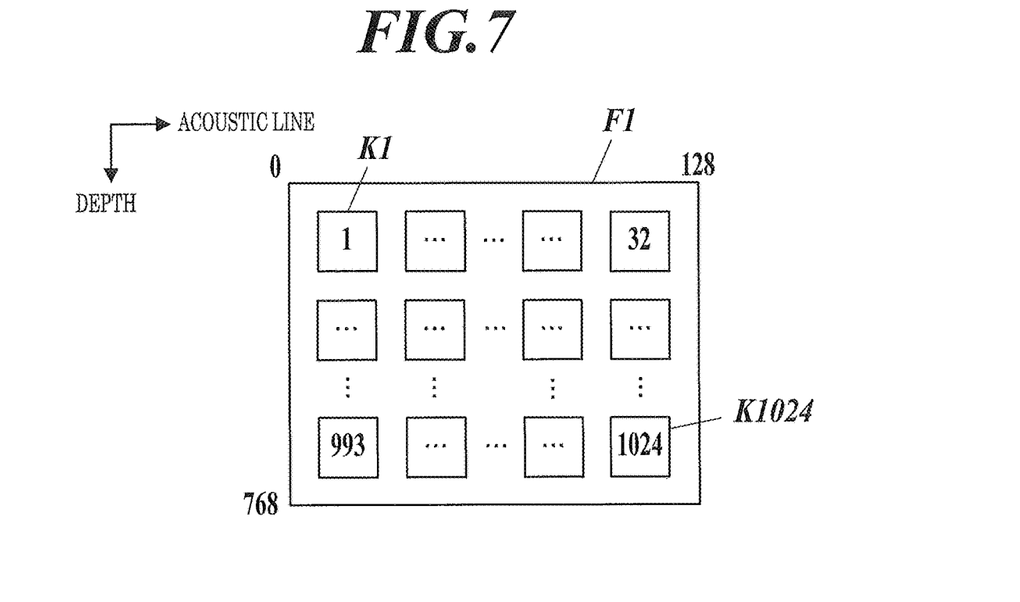
FIG. 7 shows an example of arrangement of masks in frame data of packet data.

With reference to FIG. 4 to FIG. 7, the units or the like of the MTI filter 73 are described. FIG. 4 shows a relationship between input and output of an MTI filter. FIG. 5 shows an MTI filter coefficient using orthonormal bases. FIG. 6 shows packet data having a packet size n on one frame. FIG. 7 shows an example of arrangement of masks in frame data F1 of packet data.

n complex numbers, where n represents the number of repetition (packet size), composed of the Doppler signals I, Q output from the corner turn controller 72 are referred to as packet data Sp. The packet data Sp is expressed as n input data x(0), x(1), . . . , x(n−1). The x(0), x(1), . . . , x(n−1) are arranged in the order of being generated or in its reverse order.

As shown in FIG. 4, there is no intermodulation between the clutter signal and the blood flow signal, and input and output of the MTI filter, which is a linear filter, are expressed by the following formula (1).

$$y = Ax \quad (1)$$

In the formula (1), y represents an output vector indicating packet data y(0), y(1), . . . , y(n−1) to be output from the MTI filter, A represents an MTI filter coefficient (filter matrix) (n×n), and x represents an input vector indicating input data x(0), x(1), . . . , x(n−1).

The MTI filter coefficient A for the MTI filter using orthonormal bases is, as shown in FIG. 5, generally expressed by an MTI filter coefficient $A_{reg}$ of the following formula (2).

$$A_{reg} = b \times G \times b^H \quad (2)$$

In the formula (2), b represents an orthonormal basis (n×n matrix), G represents a gain matrix (n×n matrix), and $b^H$ represents an orthonormal basis (n×n matrix) of Hermitian transpose of b.

The orthonormal bases b, $b^H$ are eigenvectors obtained, for example, by various orthogonal polynomials and principal component analysis. In the orthonormal basis b, the degree is larger as the column number is larger. In the orthonormal basis $b^H$, the degree is larger as the row number is larger. If the eigenvector obtained by principal component analysis is used as the orthonormal basis, the eigenvector with the largest eigenvalue is taken as the zero degree, and the smaller the eigenvalue is, the larger the degree is.

Diagonal elements $G_0, G_1, \ldots, G_{n-1}$ of the gain matrix G correspond to removal percentages of the MTI filter 73. A diagonal element of 0 corresponds to a removal percentage of 100%, whereas a diagonal element of 1 corresponds to a removal percentage of 0%. The diagonal elements $G_0, G_1, \ldots, G_{n-1}$ are, for examples, eigenvalues arranged in an ascending order according to the degree, and each composed of a value of 0 or 1. The values of the diagonal elements $G_0, G_1, \ldots, G_{n-1}$ are divided into 0 and 1 at the degree of a boundary corresponding to the RankCut (rank to be reduced). In this structure, the stronger the clutter removal of the MTI filter 73 is, the more the "0" is present in the diagonal elements $G_0, G_1, \ldots, G_{n-1}$. The values of the diagonal elements $G_0, G_1, \ldots, G_{n-1}$ may be numerical values between 0 and 1 inclusive.

A plurality of data on a plurality of patterns of the gain matrix G according to the strength of the clutter removal of the MTI filter 73 is stored in the storage 10.

To calculate the orthonormal bases b, $b^H$ as the eigenvectors, regions spatially adjacent to one another centering on a center point is taken as a mask, and a matrix C of a packet data set in the mask and a matrix $C^H$ of the Hermitian transpose of the matrix C are calculated. The mask is a region on a frame, the region about which a covariance matrix, described below, is calculated. As shown in FIG. 6, for example, in packet data Sp1 having the packet size n on one frame, a mask Km centering on a center point $x_m$ is set. In the packet data Sp1, planes in the depth direction and the acoustic line direction correspond to one frame, and n planes having respective repeat numbers of the one frame are arranged in a time direction. The packet data Sp1 has n frame data F1(0) to F1(n−1), where n represents the packet size.

The mask Km contains, for the packet size, input data $x_0, x_1, \ldots, x_M$ which are spatially adjacent to one another. In FIG. 6, one mask Km is shown as an example. The center position of the mask Km is a position corresponding to $x_m$. The matrix C of the packet data set of the mask Km is calculated by the following formula (3).

[Math. 1]

$$C = \frac{1}{\sqrt{M}} \begin{bmatrix} x_1(0) & \cdots & x_M(0) \\ \vdots & \ddots & \vdots \\ x_1(n-1) & \cdots & x_M(n-1) \end{bmatrix} \quad (3)$$

In the formula (3), M represents the number of points in a mask, n represents a packet size, a numeral in ( ) of input data x represents a repeat number. The matrix C of the packet data set of the mask Km is an n×M matrix.

In practice, as shown in FIG. 7, in one frame data F1 of packet data, a plurality of masks, for example, masks K1 to K1024, is set. A space between masks, the number of masks and the size of mask(s) in one frame are appropriately set. For example, in the frame of the frame data F1, the number of samples (number of lines) in the acoustic line direction is 128, the number of samples in the depth direction is 768, and the number of masks is 1,024. The packet size of the packet data shown in FIG. 7 is, for example, 16.

Under the control of the controller 9, the mask-gain setter 731 sets the space, number and size between/of masks in one frame of packet data into the covariance matrix calculator 732, and sets the gain matrix G which corresponds to the strength of the clutter removal into the MTI filter coefficient calculator 734. More specifically, the mask-gain setter 731 sets the space, number and size between/of masks in accordance with a clutter removal table 110, a frame rate table 120, both described below, and a user operation(s), and sets the gain matrix G in accordance with the clutter removal table 110 and a user operation(s).

Under the control of the controller 9, the covariance matrix calculator 732 calculates, from the packet data input from the corner turn controller 72, the matrixes C, $C^H$ of the packet data set of (the center position of) each of the masks, the space, number and size between/of which are set by the mask-gain setter 731, and calculates a covariance matrix R from the calculated C, $C^H$ of the packet data set of each of the masks by the following formula (4).

$$R = C \times C^H \tag{4}$$

Under the control of the controller 9, the eigenvector calculator 733 calculates, from the covariance matrix R of (the center position of) each of the masks input from the covariance matrix calculator 732, an eigenvector b which satisfies $Rb = \lambda b$ (where $b \neq 0$, and $\lambda$ is a scalar) and an eigenvector $b^H$ of the Hermitian transpose of the eigenvector b (orthonormal bases b, $b^H$) for each of the masks.

Under the control of the controller 9, the MIT filter coefficient calculator 734 calculates, from the gain matrix G input from the mask-gain setter 731 and the eigenvectors b, $b^H$ for (the center position of) each of the masks input from the eigenvector calculator 733, a filter coefficient (MTI filter coefficient A) for (the center position of) each of the masks of the MTI filter 73 by the formula (2).

Under the control of the controller 9, the interpolator 735 performs interpolation, such as linear interpolation or cubic interpolation, on the MTI filter coefficient A for the center position of each of the masks calculated by the MTI filter coefficient calculator 734, thereby calculating an MTI filter coefficient for each position (pixel) in the frame of the packet data input from the corner turn controller 72.

Under the control of the controller 9, the MTI filtering unit 736 calculates packet data y as complex Doppler signals by the formula (1) by using the packet data x input from the corner turn controller 72 and the gain matrix G, and outputs the calculated packet data y as the Doppler signals I, Q to the correlation operation unit 74.

Referring back to FIG. 2, under the control of the controller 9, the correlation operation unit 74 calculates, from the Doppler signals I, Q (complex Doppler signal z) filtered by the MTI filter 73, a real part D and an imaginary part N of an average value S of Doppler signal autocorrelation operation (an average value of phase difference vectors) by the following formula (5).

[Math. 2]

$$S = \sum_{k=0}^{n-1} z_k^* \cdot z_{k+1} = D + jN \tag{5}$$

Under the control of the controller 9, the data converter 75 calculates, from the Doppler signals I, Q filtered by the MTI filter 73 and the real part D and the imaginary part N of the average value S of the Doppler signal autocorrelation operation, the blood flow velocity V, the power P and the variance T. More specifically, the data converter 75 calculates the blood flow velocity V from the real part D and the imaginary part N of the average value S of the Doppler signal autocorrelation operation by the following formula (6).

[Math. 3]

$$V = \tan^{-1} \frac{N}{D} \tag{6}$$

Further, the data converter 75 calculates, from the Doppler signals I, Q (complex Doppler signal z), the power P as an average value of strength of the Doppler signals by the following formula (7).

[Math. 4]

$$P = \frac{1}{n} \sum_{k=0}^{n-1} |z_k|^2 \tag{7}$$

Further, the data converter 75 calculates, from the real part D and the imaginary part N of the average value S of the Doppler signal autocorrelation operation, the variance T as a ratio of the magnitude of the phase difference vectors to the power (but the ratio is subtracted from 1, so that the magnitude relationship is reversed) by the following formula (8).

[Math. 5]

$$T = 1 - \frac{\sqrt{D^2 + N^2}}{P} \tag{8}$$

The noise-removal spatial filter unit 76 filters the power P, the blood flow velocity V and the variance T calculated by the data converter 75. The noise-removal spatial filter unit 76 has a keyhole filter and a spatial filter (both not shown).

The keyhole filter filters the power P, the blood flow velocity V and the variance T constituting the frame of the C-mode image, thereby removing noise. In the V mode and the V-T mode, the keyhole filter removes the blood flow velocity V in a removal region(s) set by the blood flow velocity V and the power P calculated by the data converter 75, by filtering the blood flow velocity V. In the V mode and the V-T mode, the blood flow velocity V is used for image display (coloring). In the P mode, the keyhole filter removes the power P in a removal region(s) set by the blood flow velocity V and the power P calculated by the data converter 75, by filtering the power P. In the P mode, the power P is used for image display (coloring).

More specifically, in the V mode and the V-T mode, the keyhole filter assumes the blood flow signal of a region where the blood flow velocity V is smaller than a predetermined threshold value to be clutter noise and assumes the blood flow signal of a region where the power P is smaller than a predetermined threshold value to be background noise, and removes the blood flow velocity V of these regions. Further, in the P mode, the keyhole filter assumes the blood flow signal of a region where the blood flow velocity V is smaller than a predetermined threshold value to be clutter noise and assumes the blood flow signal of a region where the power P is smaller than a predetermined threshold value to be background noise, and removes the power P of these regions.

The spatial filter is a two-dimensional weighted average filter for smoothing data on the blood flow velocity V, the power P and the variance T constituting the frame of the C-mode image. In the V mode and the V-T mode, the spatial filter filters the blood flow velocity V filtered by the keyhole filter and the variance T calculated by the data converter 75. In the P mode, the spatial filter filters the power P filtered by the keyhole filter.

The inter-frame filter 77 filters, among the blood flow velocity V, the power P and the variance T filtered by the noise-removal spatial filter unit 76, the blood flow component of each frame of the C-mode image corresponding to the display mode input by the operation with the operation unit 2, so as to smooth change between the frames and leave an afterimage(s).

The C-mode image converter 78 color-codes the blood flow velocity V, the power P and the variance T filtered by the inter-frame filter 77, and convers the same into and thereby generates the C-mode image data.

Referring back to FIG. 1, the display processor 8 performs a process of constructing display image data to be displayed on the display 11 and displaying the display image data on the display 11. More specifically, if the B mode is selected, the display processor 8 performs a process of including, as an ultrasound image, the B-mode image of the B-mode image data generated by the B-mode image generator 5 in the display image data. If the C mode is selected, the display processor 8 performs a process of generating, as an ultrasound image, combined image data in which the C-mode image of the C-mode image data generated by the C-mode image generator 7 is superimposed at the position of the ROI selected on the B-mode image generated by the B-mode image generator 5, and including the combined image data in the display image data.

The controller 9 includes, for example, a CPU (Central Processing Unit), a ROM (Read Only Memory) and a RAM (Random Access Memory), and reads various programs, such as system program(s) and various process programs, stored in the ROM, loads the read programs to the RAM, and controls operation of each unit or the like of the ultrasound diagnostic apparatus 1 in accordance with the loaded programs. The RAM forms a work area where the various programs to be executed by the CPU and data on these programs are stored temporarily. The ROM includes a nonvolatile memory, such as a semiconductor, and stores the system program for the ultrasound diagnostic apparatus 1, the various process programs executable on the system program, various data and so forth. These programs are stored in the form of computer readable program codes, and the CPU operates in accordance with the program codes sequentially.

The storage 10 includes, for example, a mass storage medium, such as an HDD (Hard Disk Drive), and stores ultrasound image data (B-mode image data, C-mode image data, combined image data), the below-described clutter removal table 110, the below-described frame rate table 120, gain matrixes, frame rates (values of a frame rate) and so forth.

The display 11 is, what is called, a monitor, such as an LCD (Liquid Crystal Display) or an EL (ElectroLuminescence) display, which displays the image data output from the display processor 8.

As to each unit or the like of the ultrasound diagnostic apparatus 1, some or all of the functions of each functional block can be realized by a hardware circuit(s), such as an integrated circuit(s). The integrated circuit is, for example, an LSI (Large Scale Integration), and LSI may be called IC (Integrated Circuit), system LSI, super LSI or ultra LSI, depending on the degree of integration. The method for forming the integrated circuit is not limited to LSI, and hence the functions may be realized by a dedicated circuit(s) or a versatile processor(s), or realized by making use of an FPGA(s) (Field Programmable Gate Array(s)) or a reconfigurable processor(s) which can reconfigure connection and setting of circuit cells in LSI. Alternatively, all or some of the functions of each functional block may be performed by software. In this case, the software is stored in one or more of storage media, such as a ROM(s), an optical disk(s) and a hard disk(s), and performed by an arithmetic logic unit.

Figure 8A:
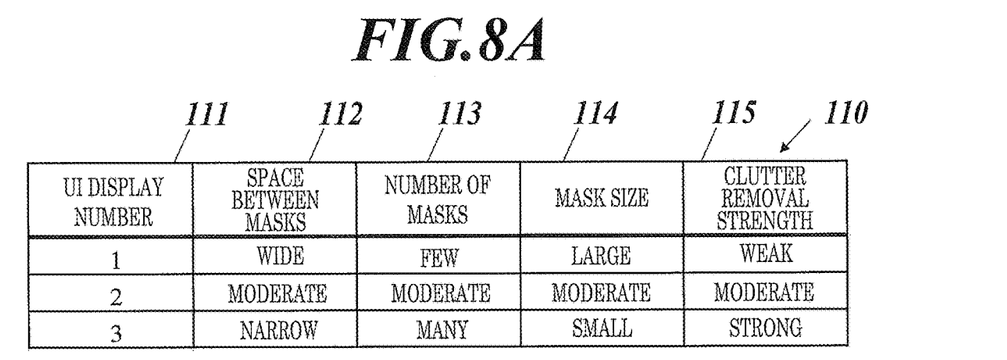
FIG. 8A shows an example of a clutter removal table.
Figure 8B:
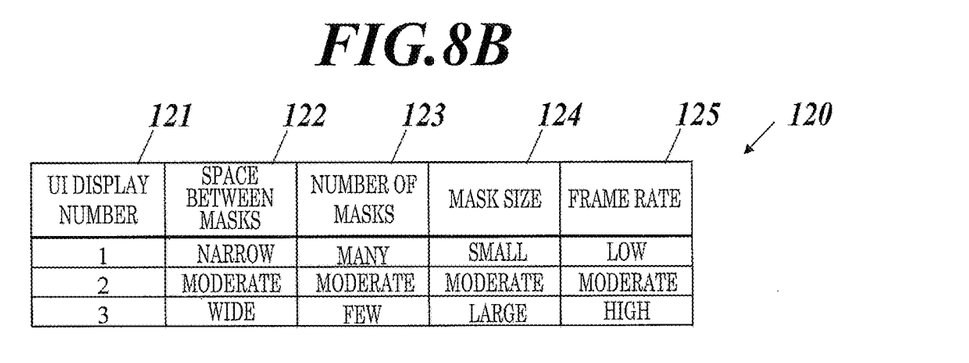
FIG. 8B shows an example of a frame rate table.

Next, with reference to FIG. 8A and FIG. 8B, the clutter removal table 110 and the frame rate table 120 stored in the storage 10 are described. FIG. 8A shows an example of the clutter removal table 110. FIG. 8B shows an example of the frame rate table 120.

As shown in FIG. 8A, the clutter removal table 110 has columns of a UI (User Interface) display number 111, a space between masks 112, a number of masks 113, a mask size 114 and a clutter removal strength 115.

The UI display number 111 is an identification number indicating the strength of the clutter removal of the MTI filter 73 with a level, and is a selected display number in a clutter removal selection region 132, described below, to be displayed. The space between masks 112 is a space between masks in one frame for the UI display number 111. The number of masks 113 is the number of masks in one frame for the UI display number 111. The mask size 114 is the size of mask(s) in one frame for the UI display number 111. The clutter removal strength 115 is information indicating the strength of the clutter removal for the UI display number 111. Gain matrixes G for the respective records of the clutter removal strength 115 are stored in the storage 10.

To set the masks, the information in the space between masks 112, the number of masks 113 and the mask size 114 is used. In the example shown in FIG. 8A, the space between masks 112 is expressed by "wide", "moderate" and "narrow", the number of masks 113 is expressed by "few", "moderate" and "many", and the mask size 114 is expressed by "large", "moderate" and "small", which are abstract. Alternatively, for example, preset numerical values may be stored in the records of the columns.

To set the gain matrix G, the information in the clutter removal strength 115 is used. In the example shown in FIG. 8A, the clutter removal strength 115 is expressed by "weak", "moderate" and "strong", which are abstract. Alternatively, for example, preset numerical values may be stored in the records of the column.

As shown in FIG. 8B, the frame rate table 120 has columns of a UI display number 121, a space between masks 122, a number of masks 123, a mask size 124 and a frame rate 125.

The UI display number 121 is an identification number indicating the frame rate of the C-mode image with a level, and is a selected display number in a frame rate selection region 133, described below, to be displayed. The space between masks 122 is a space between masks in one frame for the UI display number 121. The number of masks 123 is the number of masks in one frame for the UI display number 121. The mask size 124 is the size of mask(s) in one frame for the UI display number 121. The frame rate 125 is information indicating the frame rate for the UI display number 121. Numerical values of the frame rate for the respective records of the frame rate 125 are stored in the storage 10.

To set the masks, the information in the space between masks 122, the number of masks 123 and the mask size 124 is used. In the example shown in FIG. 8B, the space between masks 122 is expressed by "narrow", "moderate" and "wide", the number of masks 123 is expressed by "many", "moderate" and "few", and the mask size 124 is expressed by "small", "moderate" and "large", which are abstract. Alternatively, for example, preset numerical values may be stored in the records of the columns.

To set the frame rate, the information in the frame rate 125 is used. In the example shown in FIG. 8B, the frame rate 125 is expressed by "low", "moderate" and "high", which are abstract. Alternatively, for example, preset numerical values may be stored in the records of the column. In this case, the numerical values in the respective records of the frame rate 125 are used as the frame rate.

Figure 9:
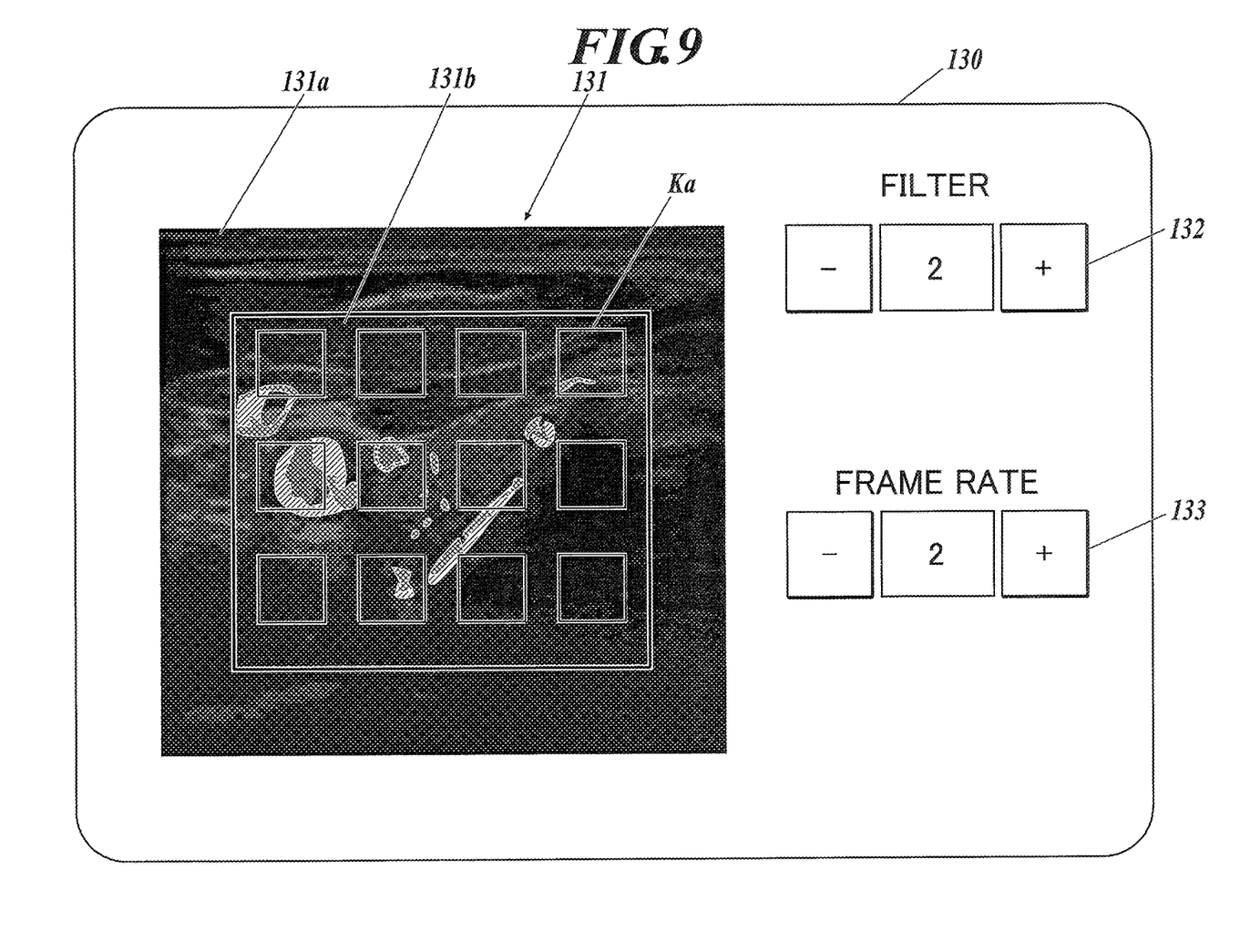
FIG. 9 shows a C-mode image display screen.
Figure 10:
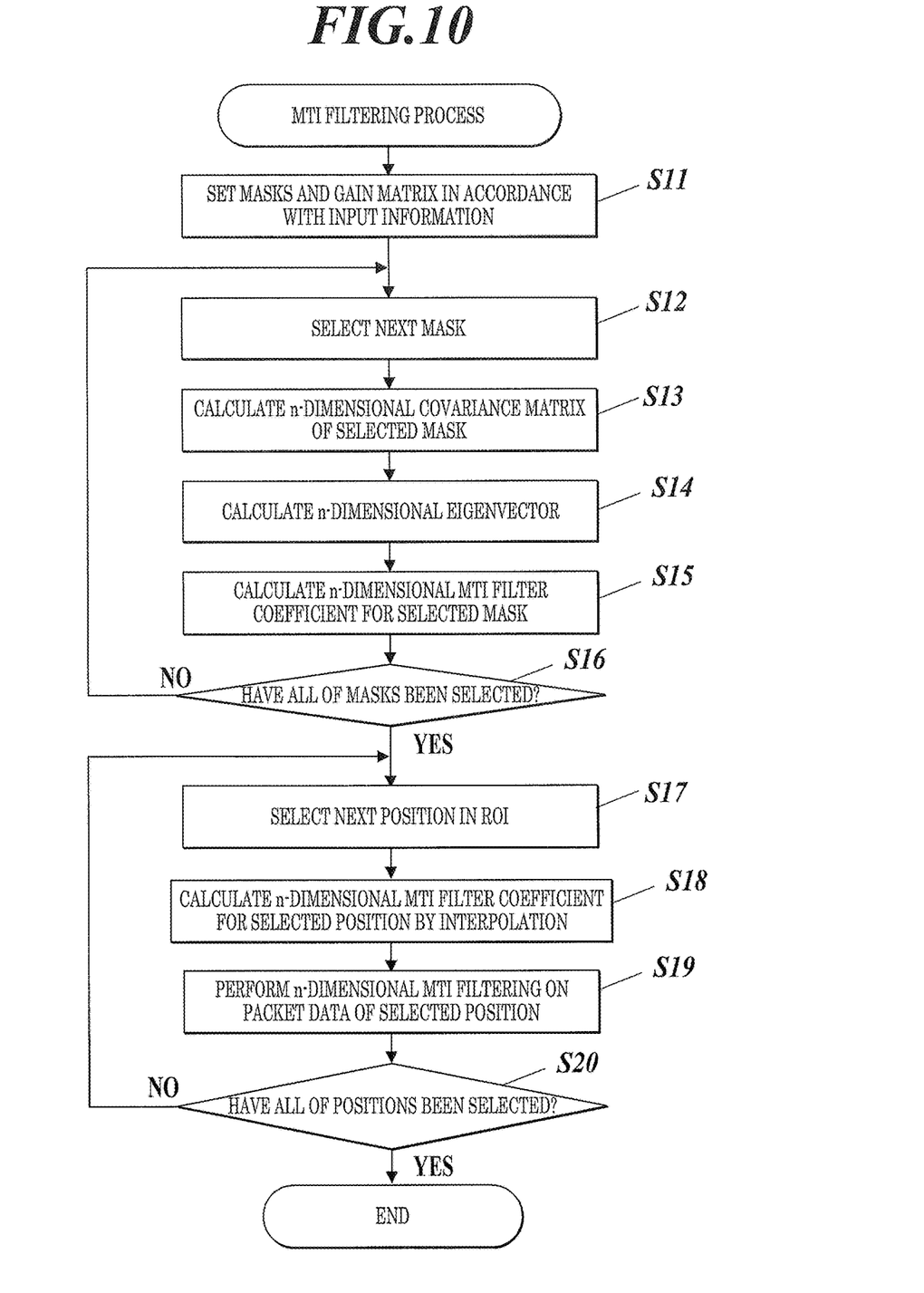
FIG. 10 is a flowchart showing an MTI filtering process according to the embodiment.
Figure 11:
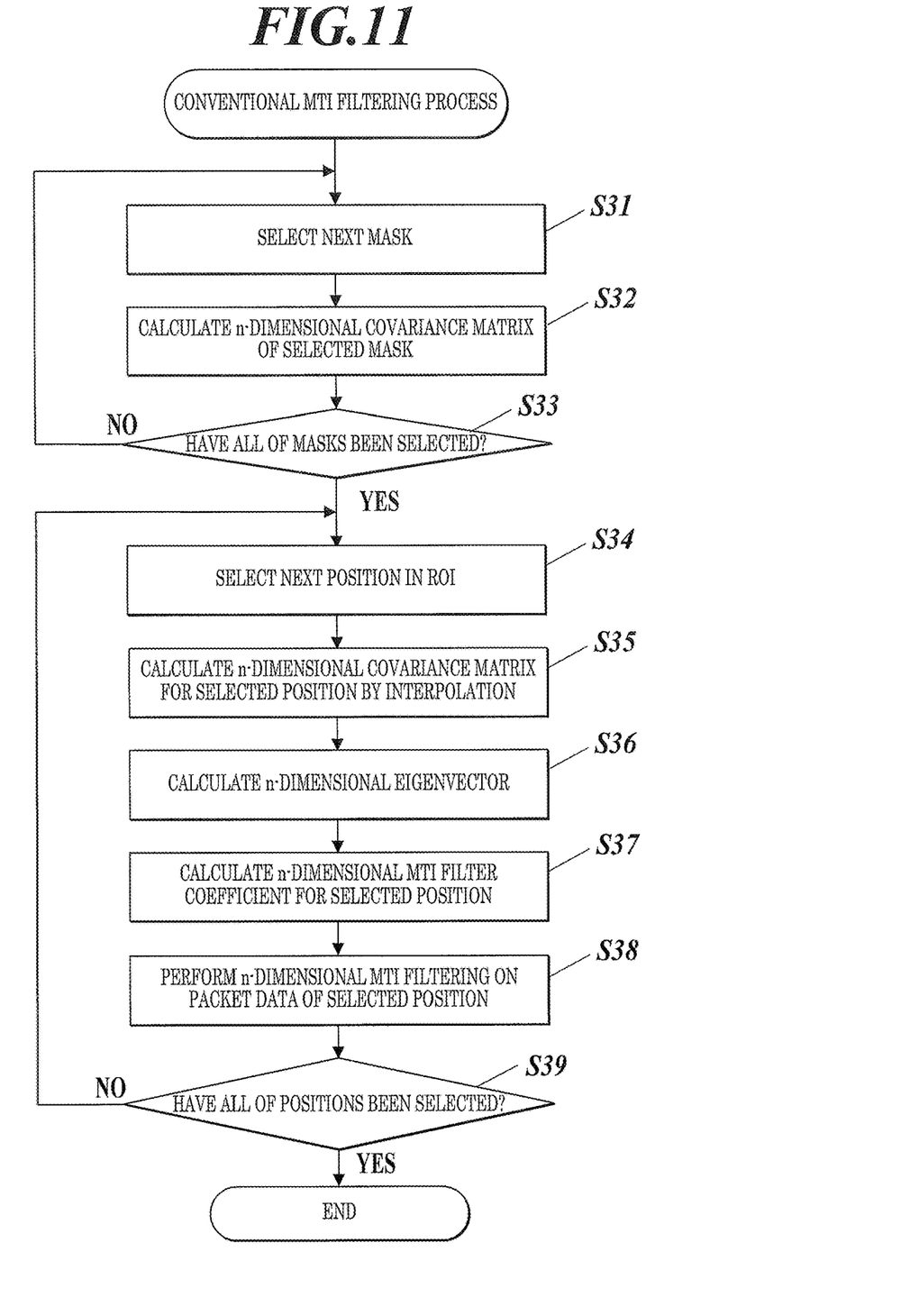
FIG. 11 is a flowchart showing a conventional MTI filtering process.

Next, with reference to FIG. 9 to FIG. 11, operation of the MTI filter 73 of the ultrasound diagnostic apparatus 1 is described. FIG. 9 shows a C-mode image display screen 130. FIG. 10 is a flowchart showing an MTI filtering process according to this embodiment. FIG. 11 is a flowchart showing a conventional MTI filtering process.

Suppose that the ultrasound diagnostic apparatus 1 is installed in a consultation room of a medical facility, and a patient and a user (examiner (doctor, technical expert, etc.)) are in the room. Further suppose that the user inputs a C-mode image display instruction, ROI specifying information and so forth via the operation unit 2, and puts the ultrasound probe 101 on the test object of the patient, and the ultrasound diagnostic apparatus 1 (controller 9) performs a C-mode image display process for displaying a C-mode image in an ROI superimposed on a B-mode image on the display 11.

In the C-mode image display process, when accepting, from the user, setting requests of the strength of the clutter removal and the frame rate input via the operation unit 2, the controller 9 displays, for example, the C-mode image display screen 130 shown in FIG. 9 on the display 11. The C-mode image display screen 130 has an ultrasound image display region 131, the clutter removal selection region 132 and the frame rate selection region 133.

The ultrasound image display region 131 has a B-mode image display region 131a and a C-mode image display region 131b. The B-mode image display region 131a is a region where the B-mode image is displayed. The C-mode image display region 131b is a region where the C-mode image is displayed by being superimposed on the B-mode image displayed in the B-mode image display region 131a. The image shown in the C-mode image display region 131b in FIG. 9 is the C-mode image in the V mode, and the blood flow velocity in a direction to be away from the ultrasound probe 101 is expressed in blue (an oblique-line pattern in the figure), and the blood flow velocity in a direction to approach the ultrasound probe 101 is expressed in red (a lattice pattern in the figure).

The clutter removal selection region 132 has: a UI display number display region where, of the UI display number 111 in the clutter removal table 110, a currently set UI display number is displayed; and + and − buttons to increase and decrease the UI display number. In the clutter removal selection region 132, the UI display number for the clutter removal displayed in the UI display number display region is increased and decreased in response to inputs made by clicking or touching the + and − buttons, respectively. For example, if the user senses that the clutter (noise) is much in the currently displayed C-mode image, he/she performs an operation to increase the UI display number in the clutter removal selection region 132 from 2 to 3, and consequently can suppress the clutter to be displayed. Meanwhile, if the user would like to increase sensitivity to the blood flow, he/she performs an operation to decrease the UI display number, and consequently can adjust the image quality. Alternatively, a number to which the UI display number for the clutter removal is changed may be directly input in the UI display number display region for the clutter removal in the clutter removal selection region 132 by the user operating the operation unit 2.

The frame rate selection region 133 has: a UI display number display region where, of the UI display number 121 in the frame rate table 120, a currently set UI display number is displayed; and + and − buttons to increase and decrease the UI display number. In the frame rate selection region 133, the UI display number for the frame rate displayed in the UI display number display region is increased and decreased in response to inputs made by clicking or touching the + and − buttons, respectively. For example, if the user senses that the frame rate is slow for the currently displayed C-mode image, he/she performs an operation to increase the UI display number in the frame rate selection region 133 from 2 to 3, and consequently can increase the frame rate. Increasing the frame rate may increase the clutter (noise). Meanwhile, if the user senses that the frame rate is sufficient, he/she performs an operation to decrease the UI display number, and consequently, in exchange of decrease in the frame rate, can suppress the clatter and adjust the image quality. Alternatively, a number to which the UI display number for the frame rate is changed may be directly input in the UI display number display region for the frame rate in the frame rate selection region 133 by the user operating the operation unit 2.

Further, as shown in FIG. 9, the controller 9 may display, in the C-mode image display region 131b, masks Ka, the space, number and size between/of which are input and set in accordance with the clutter removal selection region 132 and the frame rate selection region 133.

Next, with reference to FIG. 10, an MTI filtering process as operation of the MTI filter 73 is described. Although the MTI filtering process is a process which is performed by the controller 9 controlling the units or the like of the MTI filter 73, description of some of the control on the units or the like of the MTI filter 73 by the controller 9 may be omitted for the purpose of illustration. The MTI filtering process herein is a process for one frame of a C-mode image.

First, the mask-gain setter 731 sets the space, number and size between/of mask(s) into the covariance matrix calculator 732 and sets the gain matrix G, which corresponds to the strength of the clutter removal, into the MTI filter coefficient calculator 734 in accordance with the strength of the clutter removal and the frame rate selected and input into the clutter removal selection region 132 and the frame rate selection region 133 displayed on the display 11, the strength of the clutter removal and the frame rate being selected and input by the user via the operation unit 2 immediately before the mask-gain setter 731 sets the above (Step S11).

In Step S11, the controller 9 reads, from the clutter removal table 110 stored in the storage 10, the space between masks 112, the number of masks 113, the mask size 114 and the clutter removal strength 115 for the UI display number 111 for the clutter removal input in the clutter removal selection region 132. Further, the controller 9 reads, from the frame rate table 120 stored in the storage 10, the space between masks 122, the number of masks 123, the mask size 124 and the frame rate 125 for the UI display number 121 for the frame rate input in the frame rate selection region 133. Then, the controller 9 causes the mask-gain setter 731 to set the space between masks for the MTI filter 73 on the basis of the read spaces between masks 112, 122, the number of masks for the MTI filter 73 on the basis of the read numbers of masks 113, 123 and the size of mask(s) for the MTI filter 73 on the basis of the read mask sizes 114, 124, and reads, from the storage 10, the gain matrix G for the read clutter removal strength 115 and causes the mask-gain setter 731 to set the read gain matrix G. Further, the controller 9 sets the read frame rate into the transmitter 3 and so forth so as to set the frame rate of the C-mode image.

Next, the controller 9 selects a (or the next one) mask which has not been selected yet, from among all of the masks, set in Step S11, in one frame in the ROI (Step S12).

Next, the covariance matrix calculator 732 calculates the n-dimensional (n representing a packet size) covariance matrix R by the formulae (3) and (4) by using packet data corresponding to the mask selected in Step S12, the packet data being input from the corner turn controller 72 (Step S13). Next, the eigenvector calculator 733 calculates the eigenvectors b, b" which satisfy Rb=λb by using the n-dimensional covariance matrix R calculated in Step S13 (Step S14).

Next, the MTI filter coefficient calculator 734 calculates the n-dimensional MTI filter coefficient A for the center position of the currently selected mask by the formula (2) by using the eigenvectors b, b" calculated in Step S14 and the gain matrix G set in Step S11 (Step S15). Next, the controller 9 determines whether or not all of the masks, set in Step 11, in one frame in the ROI have been selected (Step S16). When determining that not all of the masks have been selected yet (Step S16; NO), the controller 9 proceeds to Step S12.

On the other hand, when determining that all of the masks have been selected (Step S16; YES), the controller 9 selects the next one position which has not been selected yet, from among all of the positions (pixels) in one frame in the ROI of the C-mode image (Step S17). Next, the interpolator 735 calculates the n-dimensional MTI filter coefficient for the position selected in Step S17 by interpolation by using the MTI filter coefficients A for the respective masks calculated in Step S15 (Step S18).

Next, the MTI filtering unit 736 performs n-dimensional MTI filtering on the packet data x corresponding to the position in the ROI selected in Step S17, the packet data x being input from the corner turn controller 72, by the formula (1) by using the MTI filter coefficient A calculated in Step S18, and outputs packet data y obtained by the filtering to the correlation operation unit 74 (Step S19). Next, the controller 9 determines whether or not all of the positions in one frame in the ROI have been selected (Step S20). When determining that not all of the positions have been selected yet (Step S20; NO), the controller 9 proceeds to Step S17. On the other hand, when determining that all of the positions have been selected (Step S20; YES), the controller 9 ends the MTI filtering process.

For example, the MTI filtering process of this embodiment is performed on the packet data containing the frame data F1 shown in FIG. 7. The packet size n=16. A loop of Steps S12 to S16 is repeated 1,024 times which correspond to the number of masks. A loop of Steps S17 to S20 is repeated 128×768=98,304 times which correspond to the number of positions in the ROI. Among the steps of the MTI filtering process, Step S13 for calculation of the 16-dimensional covariance matrix and Step S14 for calculation of the 16-dimensional eigenvector are those the calculation amount of which is large. That is, each of Step S13 and Step S14 is performed 1,024 times. Further, Step S15 for calculation of the 16-dimensional MTI filtering coefficient without interpolation is performed 1,024 times, and Step S18 for calculation of the 16-dimensional MTI filtering coefficient with interpolation is performed 98,304 times.

A conventional ultrasound diagnostic apparatus configured to, with an MTI filter using principal component analysis, calculate the covariance matrix, the eigenvector and the MTI filter coefficient and perform filtering performs the conventional MTI filtering process shown in FIG. 11.

For the conventional MTI filtering process, the space, number and size between/of mask(s) in one frame are preset and fixed.

Steps S31, S32, S33 and S34 in the conventional MTI filtering process correspond to Steps S12, S13, S16 and S17 in the MTI filtering process of this embodiment, respectively. In Step S35, the n-dimensional covariance matrix for the position selected in Step S34 is calculated by interpolation by using the n-dimensional covariance matrixes of the respective masks calculated in Step S32.

Steps S36, S37, S38 and S39 in the conventional MTI filtering process correspond to Steps S14, S15, S19 and S20 in the MTI filtering process of this embodiment, respectively. For example, the conventional MTI filtering process is performed on the packet data containing the frame data F1 shown in FIG. 7. A loop of Steps S31 to S33 is repeated 1,024 times which correspond to the number of masks. A loop of Steps S34 to S39 is repeated 98,304 times which correspond to the number of positions in the ROI. Step S32 for calculation of the 16-dimensional covariance matrix is performed 1,024 times. Step S36 for calculation of the 16-dimensional eigenvector is performed 98,304 times, the calculation amount of which is larger than that in the MTI filtering process of this embodiment. Further, Step S37 for calculation of the 16-dimensional MTI filtering coefficient without interpolation is performed 98,304 times, the calculation amount of which is larger than that in the MTI filtering process of this embodiment.

As described above, according to this embodiment, the ultrasound diagnostic apparatus 1 includes: the transmitter 3 which generates a drive signal for a C-mode image and outputs the drive signal to the ultrasound probe 101; the receiver 4 which obtains a reception signal from the ultrasound probe 101; the mask-gain setter 731 which sets at least one mask in a frame of packet data of the reception signal; the covariance matrix calculator 732 which calculates a covariance matrix from a plurality of packet data included in the mask of the reception signal; the eigenvector calculator 733 which calculates an eigenvector for the mask from the calculated covariance matrix; the MTI filter coefficient calculator 734 which calculates a first MTI filter coefficient for the packet data of (the center position of) the mask by using the calculated eigenvector and a gain matrix; the interpolator 735 which performs interpolation on the calculated first MTI filter coefficient so as to calculate a second MTI filter coefficient for packet data of each position in the frame; the MTI filtering unit 736 which filters the packet data of the position by using the calculated second MTI filter coefficient; and the correlation operation unit 74, the data converter 75, the noise-removal spatial filter unit 76, the interframe filter 77 and the C-mode image converter 78 which generate C-mode image data from the filtered packet data.

This, in an adoptive MTI filter using eigenvectors, can reduce calculation of the eigenvector for each position in a frame(s) and accordingly reduce calculation cost (a necessary operation/calculation memory and operation/calculation time), and also can keep high clutter removal performance because filtering is performed by using the calculated or interpolated MTI filter coefficient.

Further, the ultrasound diagnostic apparatus 1 includes the operation unit 2 which accepts an input about first information to specify mask information, and the mask-gain setter 731 sets the (at least one) mask in accordance with the mask information corresponding to the input first information. This allows the user to freely set approximate accuracy of the clutter and the frame rate of the C-mode image by operating the operation unit 2.

Further, the ultrasound diagnostic apparatus 1 includes the controller 9 which displays the set (at least one) mask on the display 11. This allows the user to visually confirm the set mask(s).

Further, the mask information includes at least one of a space between masks, the number of masks, and the size of mask(s). This allows the user to more freely set the approximate accuracy of the clutter and the frame rate of the C-mode image.

Further, the first information includes at least one of the strength of the clutter removal and the frame rate. This allows the user to make operation(s)/input(s) about at least one of the strength of the clutter removal and the frame rate and accordingly to more freely set the approximate accuracy of the clutter and the frame rate of the C-mode image.

Further, the operation unit 2 accepts an input about second information to specify the gain matrix, the mask-gain setter 731 sets the gain matrix corresponding to the input second information, and the MTI filter coefficient calculator 734 calculates the first filter coefficient by using the calculated eigenvector and the set gain matrix. This allows the user to freely set the approximate accuracy of the clutter by operating the operation unit 2.

Further, the second information includes the strength of the clutter removal. This allows the user to make an operation/input about the strength of the clutter removal and accordingly to freely set the approximate accuracy of the clutter.

Those described in the above embodiment are some of preferred examples of the ultrasound diagnostic apparatus, the ultrasound image generation method and the storage medium of the present invention, and hence not intended to limit the present invention.

For example, in the above embodiment, the controller 9 sets the space between masks, the number of masks and the size of mask(s) at the same time by using the clutter removal table 110 and the frame rate table 120 in response to operation(s)/input(s) about the strength of the clutter removal and the frame rate. However, this is not intended to limit the present invention. The controller 9 may set one or two of the space between masks, the number of masks and the size of mask(s) by using the clutter removal table 110 and the frame rate table 120 in response to operation(s)/input(s) about the strength of the clutter removal and the frame rate. Alternatively, the controller 9 may accept, from the user via the operation unit 2, operation(s)/input(s) about at least one of the space between masks, the number of masks and the size of mask(s) as the first information, and set the at least one of the space between masks, the number of masks and the size of mask(s) in accordance with this input information.

Further, detailed configurations and detailed operations of the units or the like constituting the ultrasound diagnostic apparatus 1 of the above embodiment can be appropriately modified without departing from the scope of the present invention.

Although one or more embodiments of the present invention have been described and illustrated in detail, the disclosed embodiment(s) are made for purposes of illustration and example only and not limitation. The scope of the present invention should be interpreted by terms of the appended claims.

The entire disclosure of Japanese Patent Application No. 2017-210313 filed on Oct. 31, 2017 is incorporated herein by reference in its entirety.

What is claimed is:

1. An ultrasound diagnostic apparatus comprising:
a transmitter which generates a drive signal for a C-mode image and outputs the drive signal to an ultrasound probe which transmits and receives ultrasound;
a receiver which obtains a reception signal from the ultrasound probe; and
a hardware processor which:
sets at least one mask in a frame of packet data of the reception signal;
calculates a covariance matrix from a plurality of packet data included in the at least one mask of the reception signal, wherein the at least one mask is the frame about which the covariance matrix is calculated;
calculates an eigenvector for the at least one mask from the covariance matrix;
calculates a first filter coefficient for the packet data of the at least one mask by using the eigenvector and a gain matrix;
performs interpolation on the first filter coefficient so as to calculate a second filter coefficient for packet data of each position in the frame;
filters the packet data of the position by using the second filter coefficient to define a filtered packet data; and
generates C-mode image data from the filtered packet data.

2. The ultrasound diagnostic apparatus according to claim 1, comprising an operation unit which accepts an input about first information to specify mask information, wherein
the hardware processor sets the at least one mask in accordance with the mask information corresponding to the first information.

3. The ultrasound diagnostic apparatus according to claim 2, wherein the hardware processor displays the at least one mask on a display.

4. The ultrasound diagnostic apparatus according to claim 2, wherein the mask information includes at least one of a space between the at least one mask, a number of the at least one mask, and a size of the at least one mask.

5. The ultrasound diagnostic apparatus according to claim 2, wherein the first information includes at least one of a strength of clutter removal and a frame rate.

6. The ultrasound diagnostic apparatus according to claim 1, comprising an operation unit which accepts an input about second information to specify the gain matrix, wherein
the hardware processor sets the gain matrix corresponding to the input second information, and calculates the first filter coefficient by using the calculated eigenvector and the set gain matrix.

7. The ultrasound diagnostic apparatus according to claim 6, wherein the second information includes a strength of clutter removal.

8. An ultrasound image generation method comprising:
generating a drive signal for a C-mode image and outputting the drive signal to an ultrasound probe which transmits and receives ultrasound;
obtaining a reception signal from the ultrasound probe;
setting at least one mask in a frame of packet data of the reception signal;
calculating a covariance matrix from a plurality of packet data included in the at least one mask of the reception signal, wherein the at least one mask is the frame about which the covariance matrix is calculated;
calculating an eigenvector for the at least one mask from the covariance matrix;

calculating a first filter coefficient for the packet data of the at least one mask by using the eigenvector and a gain matrix;

performing interpolation on the first filter coefficient so as to calculate a second filter coefficient for packet data of each position in the frame;

filtering the packet data of the position by using the second filter coefficient defining a filtered packet data; and generating C-mode image data from the filtered packet data.

9. A non-transitory computer readable storage medium storing a program to cause, of an ultrasound diagnostic apparatus including: a transmitter which generates a drive signal for a C-mode image and outputs the drive signal to an ultrasound probe which transmits and receives ultrasound; and a receiver which obtains a reception signal from the ultrasound probe, a computer to:

set at least one mask in a frame of packet data of the reception signal;

calculate a covariance matrix from a plurality of packet data included in the at least one mask of the reception signal, wherein the at least one mask is the frame about which the covariance matrix is calculated;

calculate an eigenvector for the at least one mask from the covariance matrix;

calculate a first filter coefficient for the packet data of the at least one mask by using the eigenvector and a gain matrix;

perform interpolation on the first filter coefficient so as to calculate a second filter coefficient for packet data of each position in the frame;

filter the packet data of the position by using the second filter coefficient, defining a filtered packet data; and generate C-mode image data from the filtered packet data.

* * * * *